(12) United States Patent
McCalmont et al.

(10) Patent No.: US 10,448,831 B2
(45) Date of Patent: Oct. 22, 2019

(54) WEARABLE SENSOR

(71) Applicants: Stephen A McCalmont, Hollis, NH (US); Stuart P MacEachern, Hopkinton, MA (US); Ralph L Beck, Sterling, MA (US)

(72) Inventors: Stephen A McCalmont, Hollis, NH (US); Stuart P MacEachern, Hopkinton, MA (US); Ralph L Beck, Sterling, MA (US)

(73) Assignee: BraveHeart Wireless Inc., Nashua, NH (US)

( * ) Notice: Subject to any disclaimer, the term of this patent is extended or adjusted under 35 U.S.C. 154(b) by 0 days.

(21) Appl. No.: 15/921,971

(22) Filed: Mar. 15, 2018

(65) Prior Publication Data

US 2018/0279881 A1 Oct. 4, 2018

Related U.S. Application Data

(60) Provisional application No. 62/479,448, filed on Mar. 31, 2017.

(51) Int. Cl.
| | | |
|---|---|---|
| *A61B 5/00* | (2006.01) | |
| *A61B 5/0205* | (2006.01) | |
| *A61B 5/11* | (2006.01) | |
| *A61B 5/145* | (2006.01) | |
| *A61B 5/024* | (2006.01) | |
| *A61B 5/08* | (2006.01) | |
| *A61B 5/053* | (2006.01) | |
| *A61B 5/0456* | (2006.01) | |
| *H04B 1/00* | (2006.01) | |
| *G16H 40/63* | (2018.01) | |
| *G16H 10/60* | (2018.01) | |

(52) U.S. Cl.
CPC ........ *A61B 5/0022* (2013.01); *A61B 5/02055* (2013.01); *A61B 5/1116* (2013.01); *A61B 5/1118* (2013.01); *A61B 5/14532* (2013.01); *A61B 5/14542* (2013.01); *A61B 5/7214* (2013.01); *A61B 5/747* (2013.01); *A61B 5/0024* (2013.01); *A61B 5/02405* (2013.01); *A61B 5/0456* (2013.01); *A61B 5/0533* (2013.01); *A61B 5/0816* (2013.01); *A61B 2560/0214* (2013.01); *G16H 10/60* (2018.01); *G16H 40/63* (2018.01); *H04B 1/00* (2013.01)

(58) Field of Classification Search
CPC .................................................. A61B 5/0022
See application file for complete search history.

(56) References Cited

U.S. PATENT DOCUMENTS

| | | | | |
|---|---|---|---|---|
| 2003/0187601 A1* | 10/2003 | Dufour | ............... | G01S 3/023 702/92 |
| 2009/0323976 A1* | 12/2009 | Asada | ............... | G10K 11/178 381/71.1 |
| 2015/0011876 A1* | 1/2015 | Bouton | ............... | A61B 5/0507 600/430 |
| 2015/0123810 A1* | 5/2015 | Hernandez-Rosas | ... | H04W 4/70 340/870.02 |
| 2015/0237461 A1* | 8/2015 | Goyal | ............... | H04B 1/385 455/41.2 |

(Continued)

*Primary Examiner* — Amine Benlagsir
(74) *Attorney, Agent, or Firm* — Maine Cernota & Rardin

(57) ABSTRACT

A wearable health sensor and methods of operating the same are herein described, the wearable health sensor and methods of operation having a variety of clinical and non-clinical uses.

18 Claims, 12 Drawing Sheets

(56) References Cited

U.S. PATENT DOCUMENTS

| | | | |
|---|---|---|---|
| 2015/0251074 A1* | 9/2015 | Ahmed | A61B 5/02405 |
| | | | 700/91 |
| 2015/0289820 A1* | 10/2015 | Miller | A61B 5/7221 |
| | | | 600/300 |
| 2015/0327808 A1* | 11/2015 | Vice | A61N 1/36014 |
| | | | 600/388 |
| 2016/0270717 A1* | 9/2016 | Luna | G06F 19/3481 |
| 2017/0172500 A1* | 6/2017 | Xiao | A61B 5/6803 |

* cited by examiner

WEARABLE SENSOR

RELATED APPLICATIONS

This application claims the benefit of U.S. Provisional Application No. 62/479,448, filed Mar. 31, 2017. This application is herein incorporated by reference in its entirety for all purposes.

FIELD OF THE INVENTION

The invention relates to medical sensors and signal reception, and, more particularly, to wearable medical sensors suitable for use in clinical and non-clinical environments and biometric signal reception and active transmission of signals on the human body for the purpose of detecting biometric indicators.

BACKGROUND OF THE INVENTION

The wearable medical device market has expanded greatly over the past decade, with consumer devices, such as the Fitbit® and Jawbone® wireless activity trackers, becoming a popular way for people to quantify and take charge of their personal fitness while rapid developments are simultaneously occurring in similar devices having a wide range of clinical uses. These devices are constantly becoming smaller, offering better battery life through both new battery chemistries and more efficient electronics, while providing more data and using better and more efficient algorithms to render that data useful.

Existing devices, however, are not yet suitable for providing all of the various types of data that may be necessary to appropriately monitor the health of a user. Where multiple types of data must be observed, different devices must often be used. In a clinical setting, this means keeping many different types of wearable medical sensors in inventory and keeping that inventory, if reusable, maintained. With batteries requiring proper care to reach their advertised lifespans, having more of such devices is likely to impact the care that each device receives.

While a number of biometric measurement techniques exist for the detection of biometric signals, one reason that prior art devices have failed to incorporate these capabilities into a single device is that interference, primarily between active (transceivers) and passive (receive only) sensors used to gather the different data types, makes accurately gathering such data quite difficult. To gather a variety of data types, these two types of sensors must be co-located on the human body, which often results in the active type sensor interfering with the passive sensor and corrupting that sensor's data. In addition, in the case of a single biometric patch configured to gather a variety of data types, many sensor types, including active and passive sensors, must be co-located in a relatively compact area, further increasing the likelihood of signal interference.

Existing devices may also require a wire between sensors worn on the user to obtain certain types of data. Such devices are susceptible to the intrusion of moisture, which can result in premature failure, potentially leaving a user without the benefit of health monitoring for some time. Existing devices are also unable to alert others as to a medical emergency, instead serving only as passive data recorders. Finally, existing devices tend to be fragile and unable to withstand significant shocks or flexing.

What is needed, therefore, are techniques for making such devices more flexible, durable and capable.

SUMMARY OF THE INVENTION

An objective of embodiments of the present disclosure is to provide a wearable health sensor that is more flexible, durable, and capable than those of the prior art.

A further objective of embodiments of the present disclosure is to enable the continuous, real-time remote monitoring of patients, with customizable alerts provided to selected care providers.

Still another object of embodiments of the present invention is to track and quantify the progress of rehabilitation efforts, giving patients meaningful feedback on their efforts and inspiring them to place additional effort into their own rehabilitation.

Still even another object of embodiments of the present invention is to allow for the creation of local and cloud-based repositories of patient data for later review and analysis, thereby providing valuable insights into trends and patient health that might not otherwise be noticeable during routine caregiver visits, while providing medical researchers vast amounts of potentially useful clinical information that may enable medical breakthroughs through, among other potential methods, the application of big data analytics.

A still even further objective of embodiments of the present disclosure is to improve caregiver efficiency by reducing or eliminating the need for the measurement of vital signs during patient visits.

Still yet another objective of embodiments of the present disclosure is to improve on the durability of current wearable medical devices.

A still yet further objective of embodiments of the present disclosure is to reduce the number of clinical wearable sensors that need to be kept in inventory by hospitals and other medical facilities using such devices.

An even still further objective of embodiments of the present disclosure is to enable the use of a variety of active and passive sensors co-located on a wearable sensor or sensors placed, during use, on a body, by providing a method of synchronization that eliminates or reduces the risk of data corruption by active sensors.

One embodiment of the present disclosure provides a wearable health monitor comprising: at least one active sensor; at least one passive sensor; and a synchronization module configured to synchronize outputs from the at least one active sensor such that the impact of those outputs on data received by the at least passive sensor is minimized.

Another embodiment of the present disclosure provides such a wearable health monitor wherein the synchronization module employs a multiplexing schema selected from the group consisting of Frequency Division Multiple Access (FDMA), Code Division Multiple Access (CDMA), Orthogonal Frequency Division Multiple Access (OFDMA), and Spatial Division Multiple Access (SDMA).

A further embodiment of the present disclosure provides such a wearable health monitor wherein the synchronization module employs time division multiplexing.

Yet another embodiment of the present disclosure provides such a wearable health monitor wherein the at least one active sensor is assigned at least one time slot in which to transmit a signal that corresponds with a repeating period of relatively-constant signal reception by the at least on passive sensor.

A yet further embodiment of the present disclosure provides such a wearable health monitor further comprising a connection module configured to wirelessly connect the wearable health monitor to a wireless network and thereby enable the sharing of data generated by the wireless sensor.

Still another embodiment of the present disclosure provides such a wearable health monitor wherein the connection module is selected from the group consisting of a Bluetooth® module, an 802.11x wireless module, a cellular modem, and a Near Field Communication module.

A still further embodiment of the present disclosure provides such a wearable health monitor wherein the connection module is configured to allow the wearable health monitor to connect to a user device.

Even another embodiment of the present disclosure provides such a wearable health monitor wherein the user device is a cellular phone.

An even further embodiment of the present disclosure provides such a wearable health monitor wherein the at least one active sensor comprises an Electro Dermal Activity (EDA) sensor.

A still even another embodiment of the present disclosure provides such a wearable health monitor wherein the wearable health monitor is configured to monitor heart rate, heart rate variability, steps taken, respiratory rate, blood oxygen levels, skin temperature, body posture, glucose levels, and galvanic skin response/electro dermal activity.

Still yet another embodiment of the present disclosure provides such a wearable health monitor further comprising an inductive charging module configured to allow inductive charging of a power source configured to power the wearable health monitor.

A still yet further embodiment of the present disclosure provides such a wearable health monitor further comprising an event button.

Even yet another embodiment of the present disclosure provides such a wearable health monitor wherein the event button is configured, when activated, to perform a function selected from the group consisting of record data, alert emergency responders, and mark the data being recorded at that time for later review.

An even yet further embodiment of the present disclosure provides such a wearable health monitor wherein the event button is configured to be triggered remotely, through a smartphone application.

One embodiment of the present disclosure provides a system of wearable health monitors comprising: at least two wearable health monitors, each monitor comprising: at least one active sensor; at least one passive sensor; and a synchronization module configured to synchronize outputs from the at least one active sensor such that the impact of those outputs on data received by the at least passive sensor is minimized; wherein at least one wearable health monitor is configured to transmit a signal, during use, through a body of a user, and at least one wearable health monitor is configured to receive the signal.

Another embodiment of the present disclosure provides such a system of wearable health monitors wherein the at least two wearable health monitors are configured to self-configure, as master/slave nodes or peer to peer nodes, dependent on network requirements.

A further embodiment of the present disclosure provides such a system of wearable health monitors wherein at least two health monitors are configured to gather overlapping data, to compare that data, and to normalize that data by omitting erroneous data and averaging non-erroneous data.

Yet another embodiment of the present disclosure provides such a system of wearable health monitors further comprising a wideband noise sensor.

A yet further embodiment of the present disclosure provides such a system of wearable health monitors wherein the system comprises at least 5 wearable health monitors and wherein the wearable health monitors are configured to provide reverse phase noise cancellation functionality.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
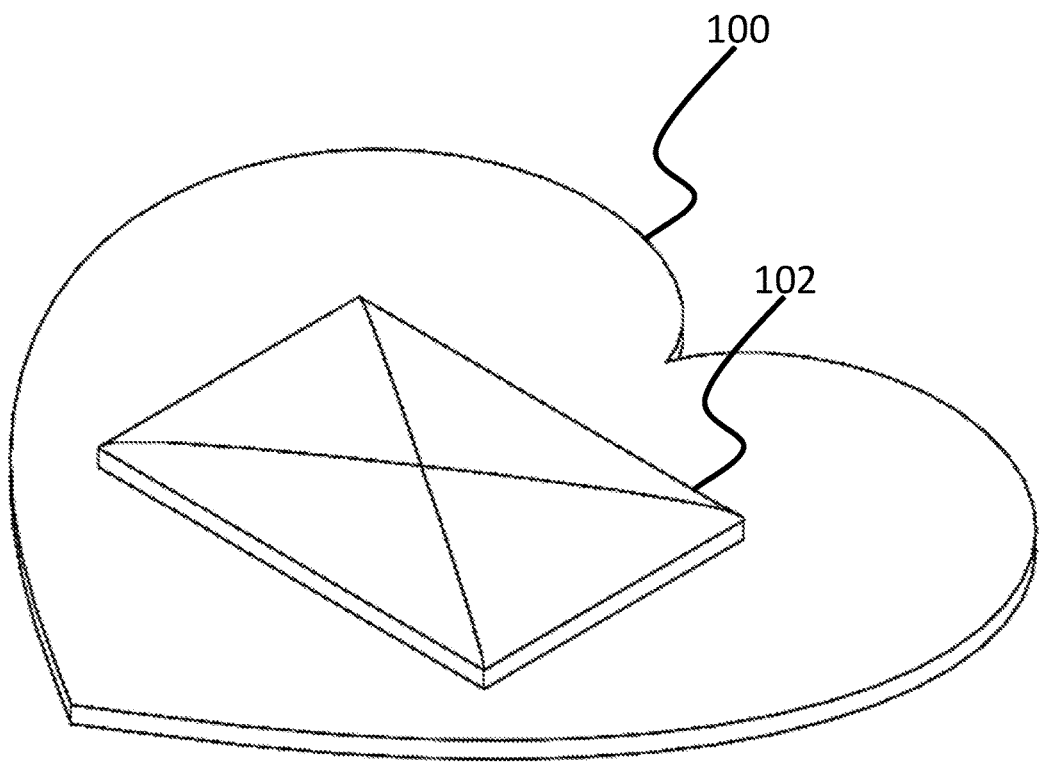
FIG. 1 is an isometric view of a wearable health sensor, configured in accordance with embodiments of the present disclosure.

Now referring to FIG. 1, an isometric view of a wearable health sensor 100, configured in accordance with embodiments of the present disclosure, is shown. Such a wearable health sensor 100 may include a housing 102 containing circuitry necessary to the operation of the sensor.

Figure 2:
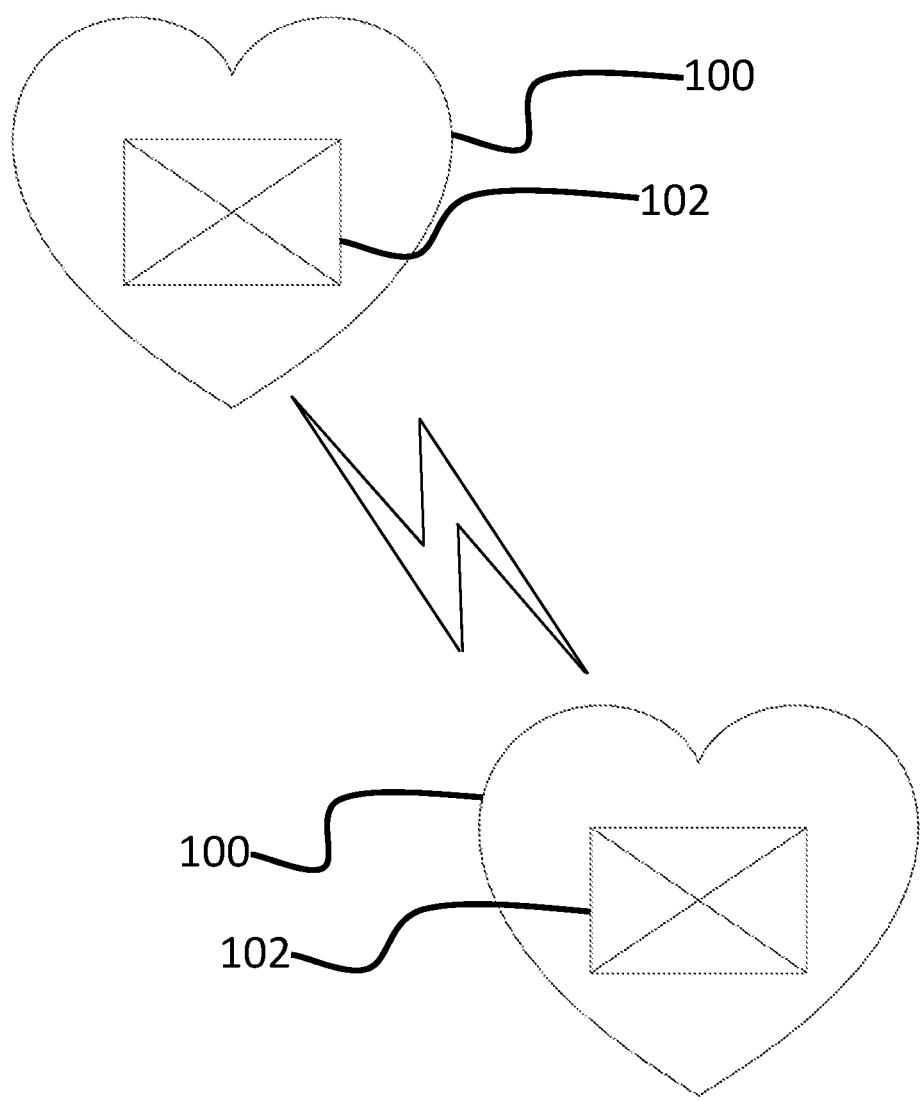
FIG. 2 is a depiction of two wearable health sensors in operative communication with one another, in accordance with embodiments of the present disclosure.

Now referring to FIG. 2, two wearable health sensors 100 are shown in operative communication with one another. Such operative communication may be in the form of an ad-hoc, mesh, or other network. Wearable health sensors 100 comprising such networks may be configured, or self-configure, as master/slave nodes or peer to peer nodes, among other potential configurations. In embodiments, Industrial, Scientific and Medical (ISM) radio bands may be used for such purposes, although most 802.15.x or similar network protocols would also be suitable.

Figure 3:
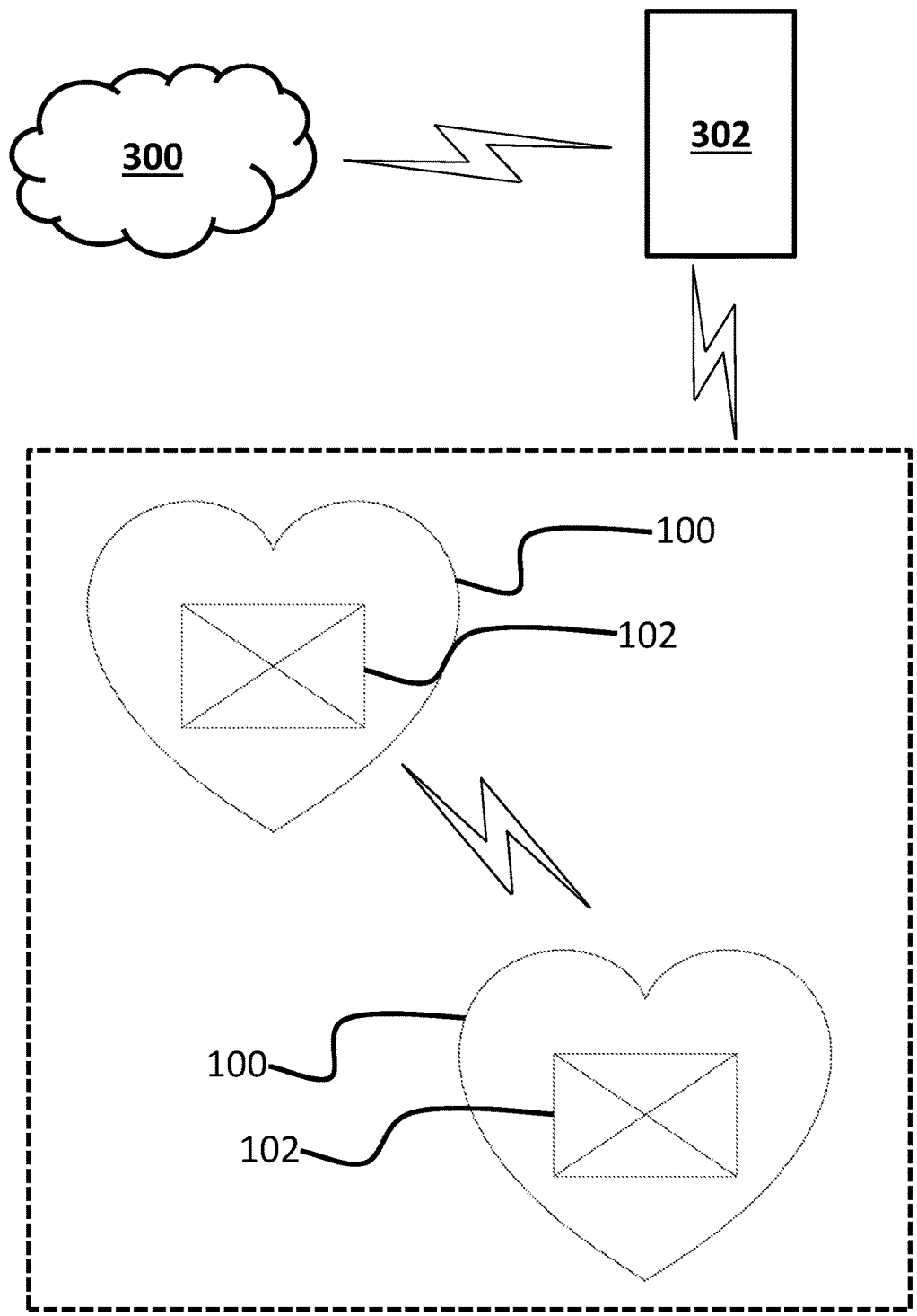
FIG. 3 is a depiction of two wearable health sensors in operative communication with one another and in further operative communication with an internet-enabled device configured to provide network access to the wearable health sensors, in accordance with embodiments of the present disclosure.

Now referring to FIG. 3, two wearable health sensors 100 are shown in operative communication with one another and in further operative communication with a network-enabled device 302, which may, in embodiments, be in further communication with a network 300. In embodiments, this network 300 may be a local-area network, such as might be used in a hospital setting for intra-hospital communications, while in other embodiments this network 300 may be a wide-area network, such as the internet. Such communication between wearable health sensors may be enabled via Bluetooth®, WiFi, cellular data, or a number of other means, which would be known to one of ordinary skill in the art.

Figure 4:
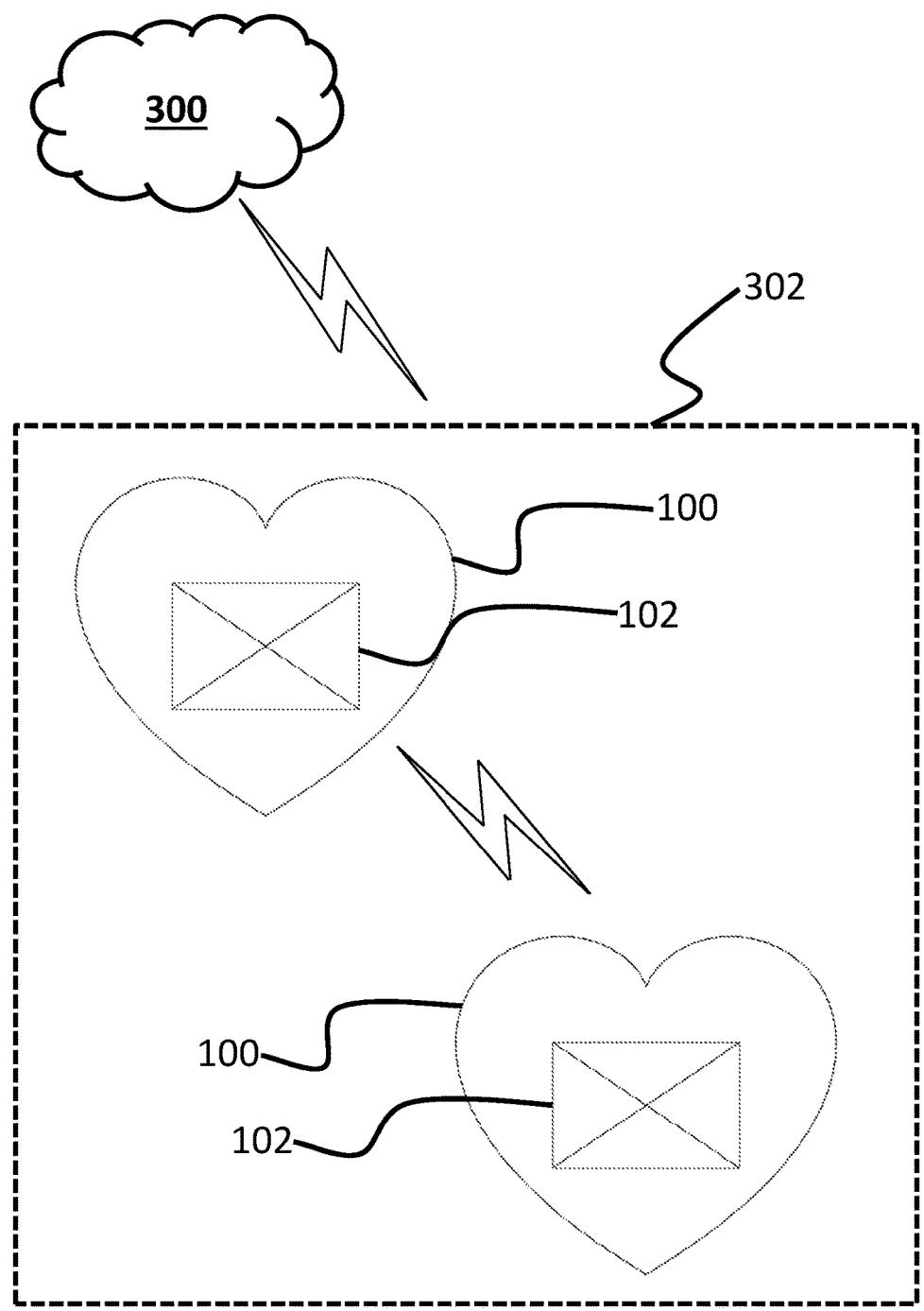
FIG. 4 is a depiction of two wearable health sensors in operative communication with one another and in further operative communication with a network, in accordance with embodiments of the present disclosure.

Now referring to FIG. 4, two wearable health sensors 100 are shown in operative communication with one another and in further operative communication directly with a network 300. Such communication may be enabled in a variety of ways, such as by the inclusion of a cellular data-capable modem and/or a WiFi enabled chipset in the wearable health sensors 100, although other methods of enabling network access would be known to one of ordinary skill in the art.

Figure 5:
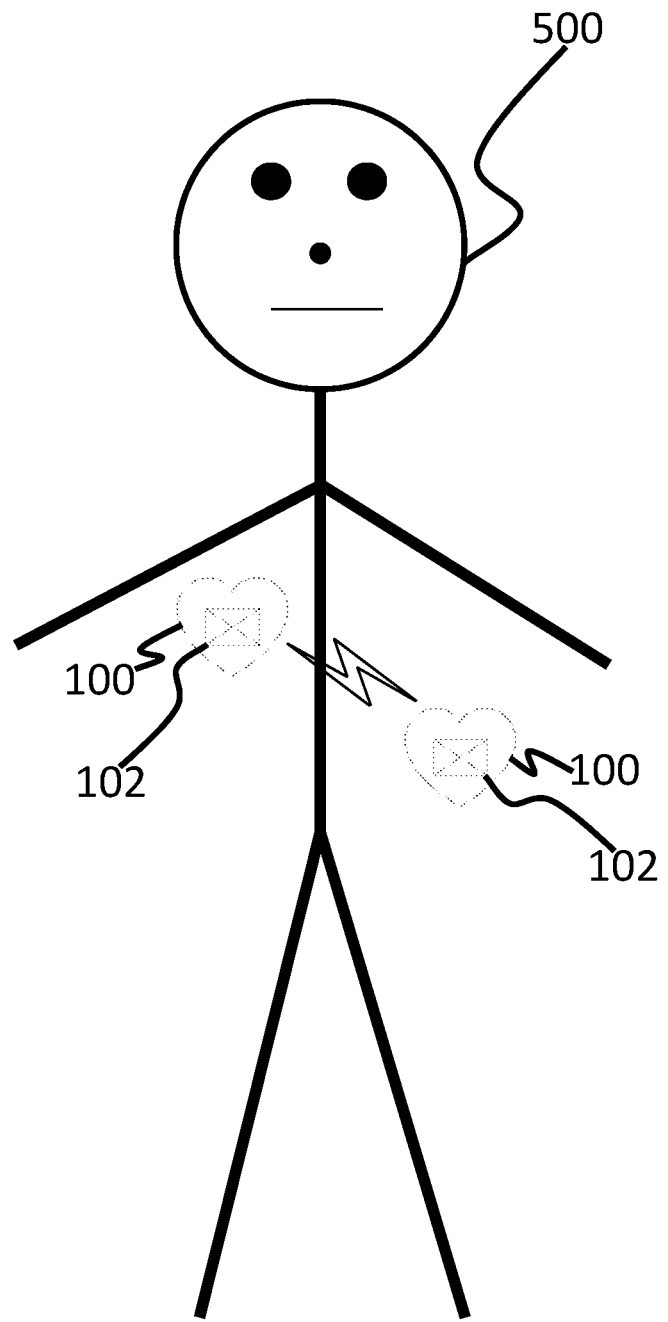
FIG. 5 is a depiction of two wearable health sensors affixed to a user, in accordance with embodiments of the present disclosure.

Now referring to FIG. 5, a user 500 is shown wearing two wearable health sensors 100, which are in operative communication with one another. Wearable health sensors 100 configured in accordance with such embodiments are capable of ascertaining their distance relative to one another as well as their position on a user, enabling the recording of data that no one sensor could easily or reliably ascertain, such as wearable health sensors 100 worn on opposite sides of an abdomen to measure respiration response. Such wearable health sensors 100 may be paired to one another by any appropriate means, such as through Bluetooth®, thereby allowing the wearable health sensors 100 to ascertain that they are worn on the one user 500 and their approximate position on such user 500.

Embodiments may further provide a user 500 feedback regarding the distance between wearable health sensors 100 and the location of those sensors 100 on the user 500. Such feedback may be in the form of vibratory pulses that become more closely spaced as the optimal distance and location are reached or may comprise a visual indication provided by an application running on a device connected to such sensor(s) 100. Other suitable means of providing user feedback would be well known to one of ordinary skill in the art.

In still even other embodiments, a third wearable health sensor 100 may be used as a reference point. For instance, a user 500 may be instructed to place a reference wearable health sensor 100 on an-easy to determine region of their body, such as end of the person's breastbone, where the ribs come together. Using the location of the reference wearable health sensor 100, the approximate location of other wearable health sensors 100 may then be inferred.

In other embodiments, any number of wearable health sensors 100 may be combined, in some embodiments through the use of a mesh network.

Figure 6:
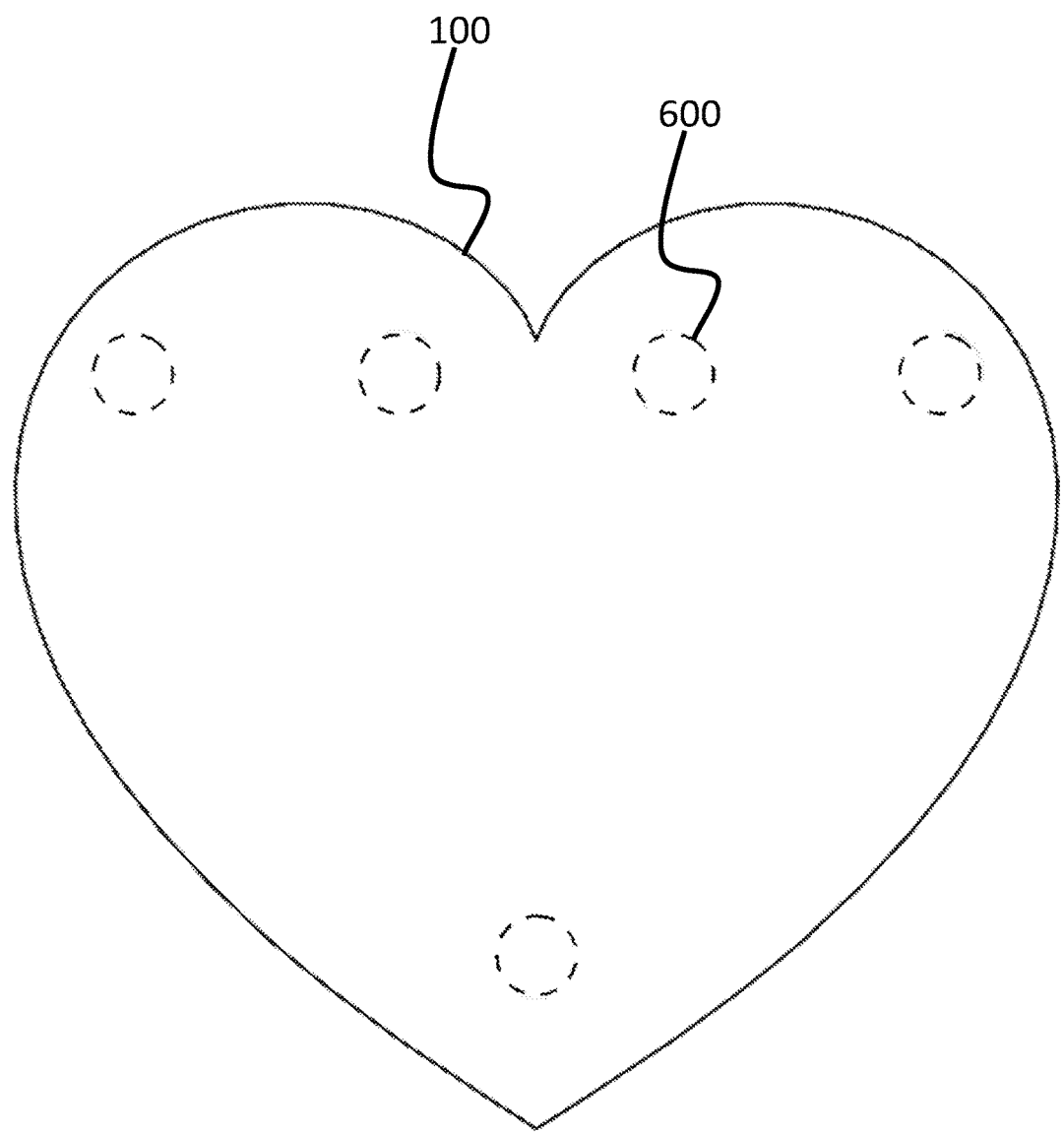
FIG. 6 is a bottom plan view of a wearable health sensor showing potential sensor locations, configured in accordance with embodiments of the present disclosure.

Now referring to FIG. 6, a bottom plan view of a wearable health sensor 100 showing potential sensor locations 600, configured in accordance with embodiments of the present disclosure, is depicted. In embodiments, one or more of these sensor locations 600 may be used.

Figure 7:
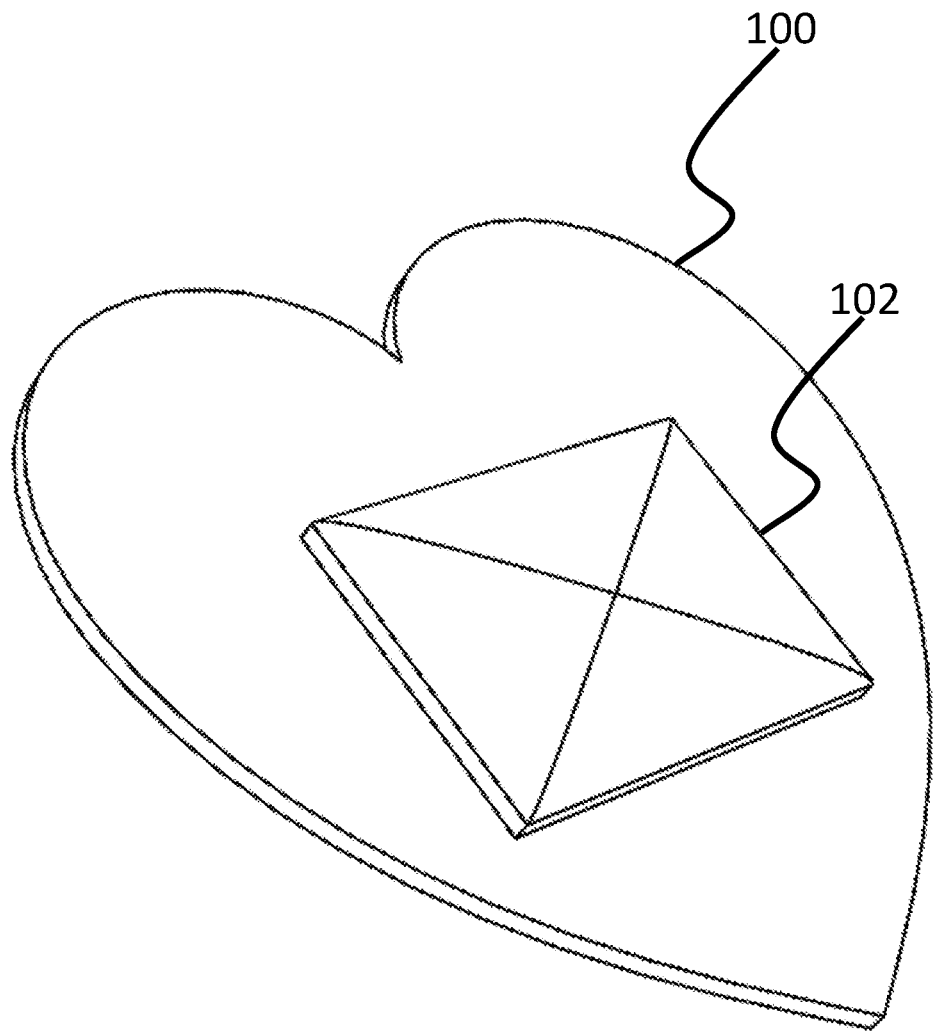
FIG. 7 is a front, top, left-side perspective view of a wearable health sensor, configured in accordance with embodiments of the present disclosure.

Now referring to FIG. 7, a front, top, left-side perspective view of a wearable health sensor 100, configured in accordance with embodiments of the present disclosure, is shown, complete with a housing 102 containing circuitry necessary to the operation of the sensor.

In various embodiments of the present disclosure, more than one type of data may be taken and communicated by the wearable health sensor 100 or a network of such wearable health sensors 100. In such embodiments, such data may be multiplexed, enabling the communication of multiple electronic messages over a single communications pathway, either wired or wireless. This allows multiple biosensor parameters to communicate through one communications pathway, such as one pair of wires, compared with having several communications pathways or wires to accomplish the same job. Non-multiplexed systems would typically require four to five wires per biometric sensor.

Figure 8:
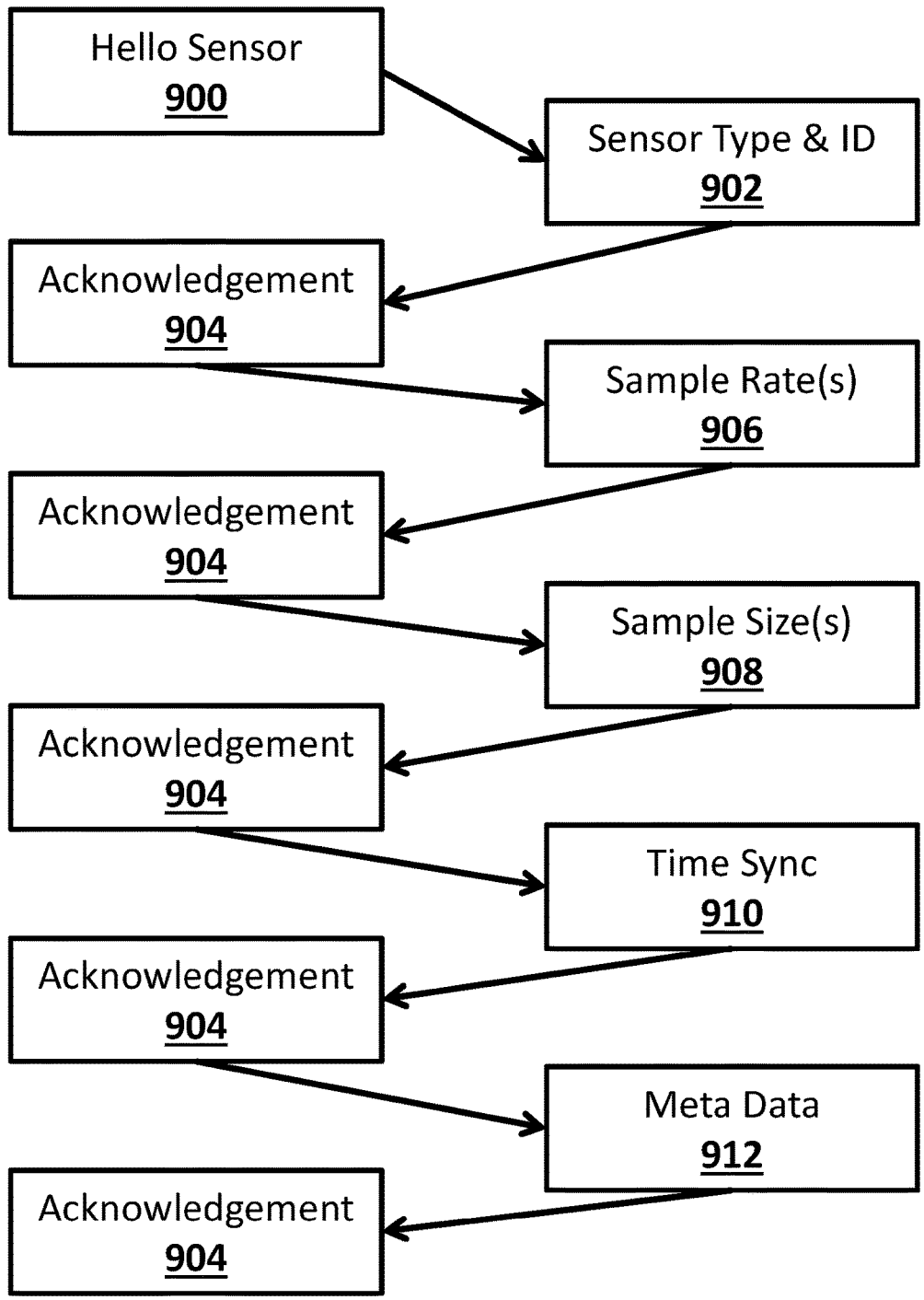
FIG. 8 is a diagram showing the exchange of data between devices configured in accordance with embodiments of the present disclosure.

Now referring to FIG. 8, the flow of information between devices configured in accordance with embodiments of the present disclosure is illustrated. In this illustration, a controller, which may be a wearable health sensor 100 in accordance with embodiments of the present disclosure, is engaged in communications with a wearable health sensor 100. The controller first polls 900 the wearable health sensor 100 and the wearable health sensor responds with its sensor type and ID 902. After the controller acknowledges receipt of this data 904, the wearable health sensor 100 provides its supported sample rate 906. This communication between controller and sensor continues in this manner until all relevant data is obtained. In addition to the above-noted relevant data, relevant data may include: sample size 908, time synchronization 910, and transfer of metadata 912.

Figure 9:
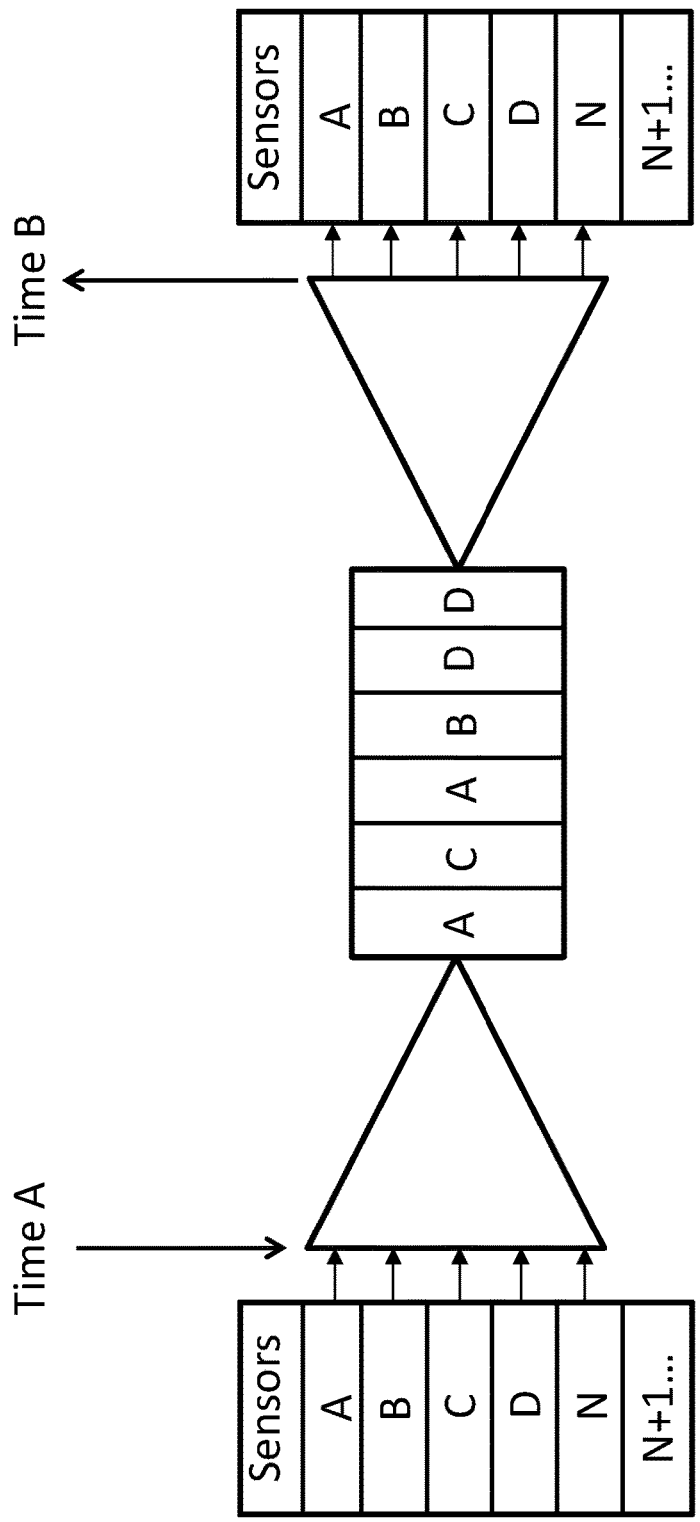
FIG. 9 is a diagram showing a multiplexing schema and associated signal representations, in accordance with embodiments of the present disclosure.

Now referring to FIG. 9, a multiplexing schema is shown alongside signal representations indicating the shape of various waveforms that might be generated by the various sensor types of the wearable health sensor(s) 100 and transmitted in accordance with the multiplexing schema. Although the multiplexing schema illustrated is a Time Division Multiplexing Access (TDMA) schema, most any multiplexing schema could be used. Some such suitable multiplexing schemas are Frequency Division Multiple Access (FDMA), Code Division Multiple Access (CDMA), Orthogonal Frequency Division Multiple Access (OFDMA), and Spatial Division Multiple Access (SDMA).

Figure 10:
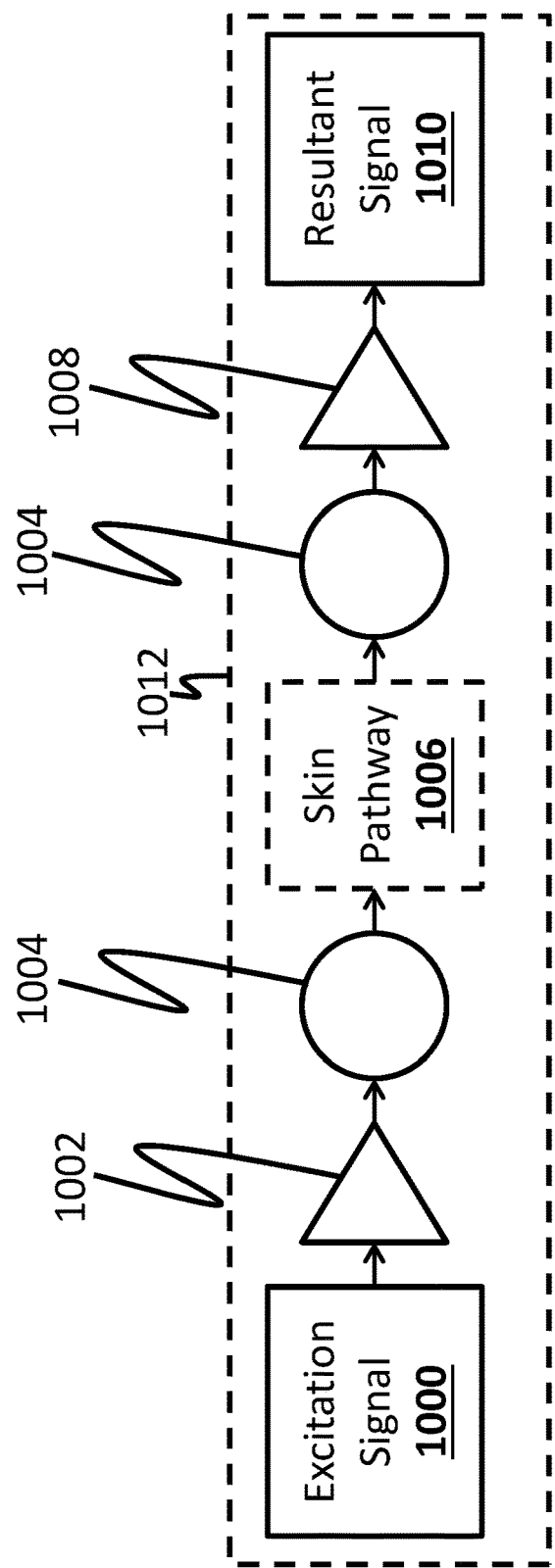
FIG. 10 is a schematic showing an active sensor configured to measure in accordance with embodiments of the present disclosure.

Now referring to FIG. 10, the structure of an active sensor 1012 configured to measure Electro Dermal Activity (EDA), AKA Galvanic Skin Response, is shown schematically. This sensor comprises an excitation signal module 1000 that is transmitted, using a transmitter 1002, through skin contact sensors 1004 that create a skin pathway 1006, to a receiver 1008 that conveys the signal to a resultant signal module 1010, which is configured to receive the excitation signal 1000. In embodiments, the excitation module 1000 is configurable based on the sensor type and the resultant signal module 1010 is programmable based on the receive signal type.

Figure 11:
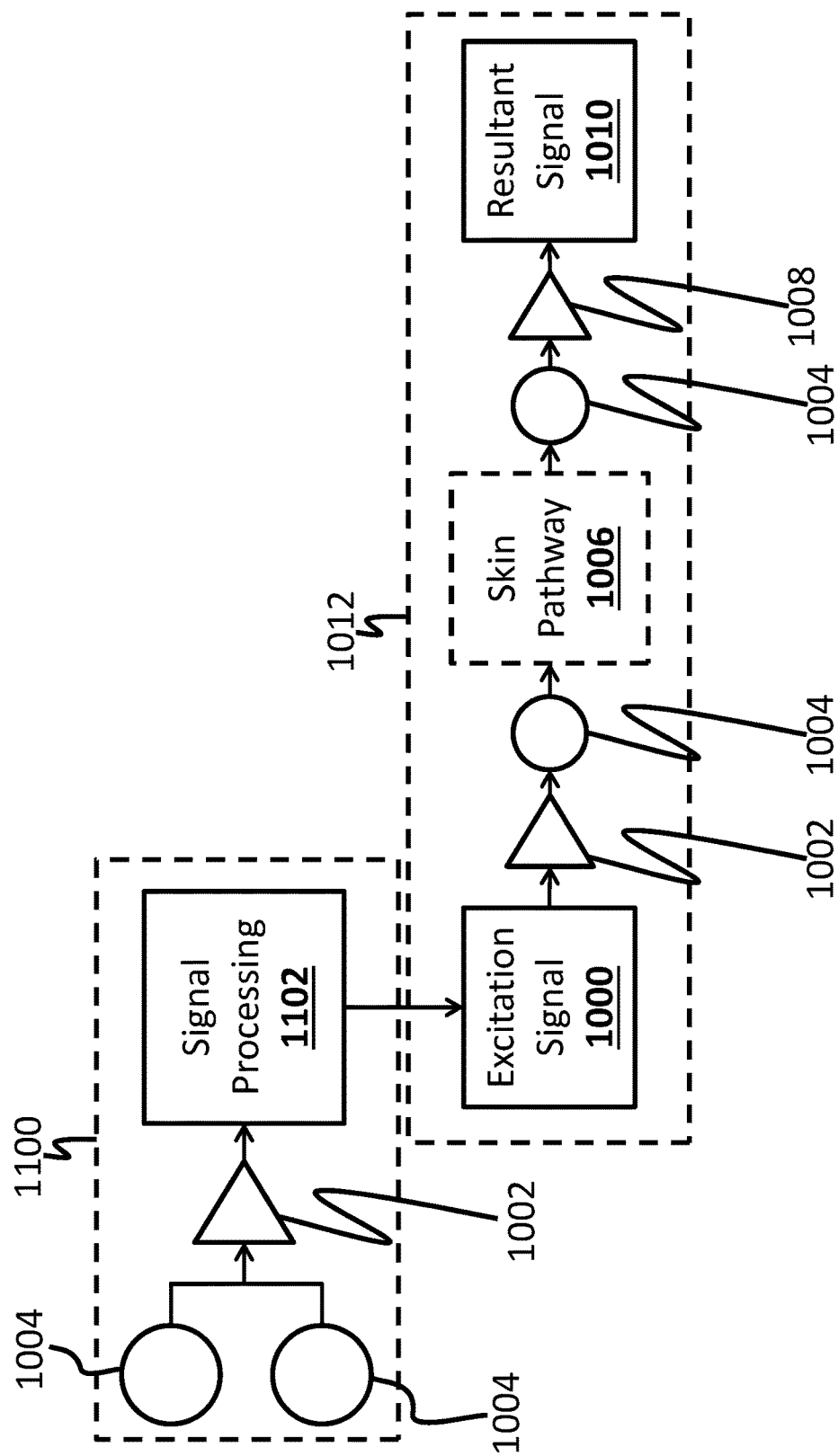
FIG. 11 is a block diagram showing a passive differential receiver sensor coupled with an active sensor, in accordance with embodiments of the present disclosure.

Now referring to FIG. 11, a block diagram showing a passive differential receiver sensor 1100 comprising two skin contact sensors 1004, a transmitter 1002, and a signal processing module 1102 coupled with an active sensor 1012, in accordance with embodiments of the present disclosure. In embodiments, the process of the active sensor is designed such that it does not interfere with the receive signal. This is done by analyzing the receive signal 1000 and controlling the active sensor 1012 in such a way as to not corrupt key parts of the resultant signal 1010.

Figure 12:
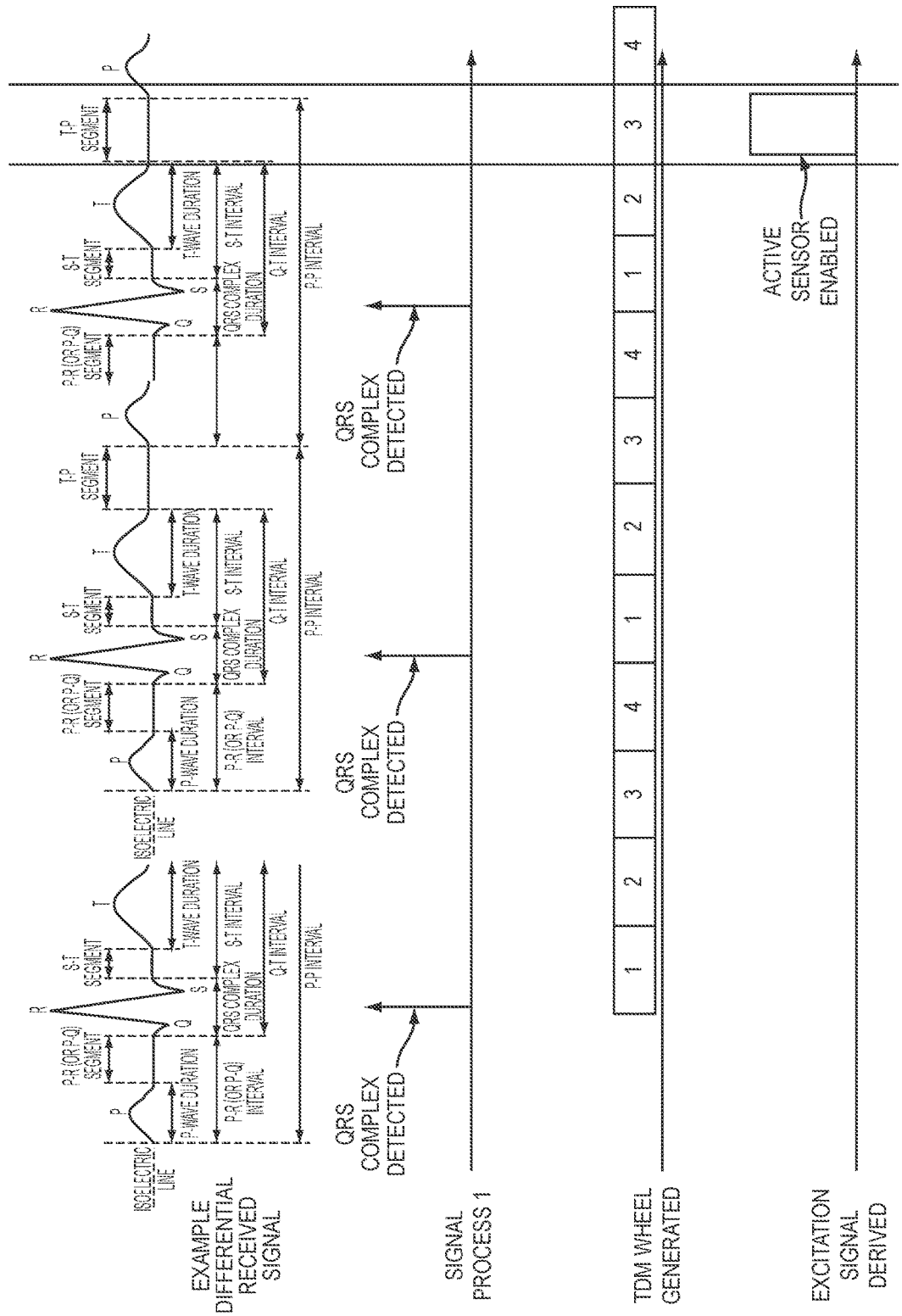
FIG. 12 is a graph showing signal inputs, outputs, and processing of a detection and synchronization apparatus in accordance with embodiments of the present disclosure.

FIG. 12 comprises a graph showing signal inputs, outputs, and processing of a detection and synchronization apparatus in accordance with embodiments of the present disclosure. In this graph, particularly the example differential received signal portion thereof, it can be seen that the received signal can be broken down into repeating segments, with some segments overlapping. In this case, the repeating signal is an EKG signal and the repeating segments are the PR Interval, PR Segment, QRS Complex, QT Interval, ST Segment, and TP Segment, with specific points on that segment being labeled P, Q, R, S, and T, in order of appearance in the repeated signal. In embodiments of the present disclosure, the received signal is analyzed for repeating segments and, once such a repeating segment is found, it is used to generate a TDM wheel. In embodiments, active sensor(s) are assigned to periods where the received signal is relatively constant. In embodiments, this relatively-constant portion of the signal is the TP Segment of an EKG signal. Assigning the active sensor to such periods of relatively-constant signal allows for the use of both passive and active sensors simultaneously without interference.

Various embodiments also support data normalization. For instance, where multiple wearable health sensors 100 are used and gathering overlapping information, the data may be compared and erroneous data identified and omitted or data averaged to obtain superior accuracy and reduce the transmission of redundant data.

Embodiments may further use data packing techniques to maximize the use of network bandwidth and ensure data integrity.

Embodiments of the wearable health sensor 100 also support demultiplexing of information, which, in many cases, is necessary for such information to be input to legacy machinery. This is because relatively old clinical equipment, which comes with a large initial expense and learning curve, relies on data being input in a specific format. Typically, such equipment is not capable of parsing multiplexed data on its own. The up-front cost of new equipment and the continued viability of the legacy equipment requires such a solution to allow new technology, such as that described herein, to be adopted in many clinical settings.

Embodiments of the wearable health sensor 100 utilize an event button. Such an event button may be considered to be a trigger that can do multiple things, such as record data, alert emergency responders, mark the data being recorded at that time for later review, etc. While this button is, in embodiments, a physical button, in other embodiments, it is a virtual button that can be activated by a volitional movement. In still other embodiments, the event button is triggered by certain patterns of data. In even still other embodiments, the event button can be triggered remotely, for example, through an application, such as that used on a smartphone.

In embodiments, the wearable health sensor 100 may be paired to a network-connected device 302, such as a smartphone 302 or wireless router 302 to allow data to be sent and received from the internet 300 or cloud 300. While some embodiments require the wearable health sensor to be paired to a network-connected device 302, other embodiments are able to connect directly to such networks, by cellular data modem or other methods as would be known to one of ordinary skill in the art.

Embodiments further support signal addition and subtraction across multiple wearable health sensors 100.

In embodiments, the wearable health sensor 100 may be hermetically sealed. In such embodiments, inductive charging may be used to enable use following exhaustion of the power source's original charge. Alternative, embodiments are disposable and are manufactured with a pre-charged power source.

Embodiments may utilize one or more thin flexible circuit boards, onto which all necessary electronics are attached.

Embodiments may further employ noise cancellation for multi-sensor 100 environments. In embodiments, noise cancellation may be achieved through the use of a wideband noise sensor, which is used to provide a measure of the background noise, combined with noise-cancelling algorithms. In some embodiments five sensors 100 may be used to provide reverse phase noise cancellation capabilities.

Still even yet other embodiments utilize software-defined sensors 100. In such embodiments, a single universal sensor 100 is programmed to provide whatever information may be necessary to serve in a given application. This may be accomplished through the use of filters. Since processing power and the capacity of onboard power sources will typically be limited, such processing, in embodiments, occurs in the cloud.

Still even yet other embodiments allow triggering and personalization of alarms based on patterns and/or groups of patterns received from the sensor(s) 100.

Still even other embodiments provide personalization templates, which may be considered alarms specific to people and/or groups of people. Such alarms may be configured, in various embodiments, by the user 500, a physician, a group of users, etc.

Still other embodiments conduct analysis of the data collected from a user 500, specific groups of users 500, or all users 500 and attempt to correlate incidents, such as cardiac arrest, to patterns in the data prior to the event. Embodiments may personalize the detection of such events to a particular user 500 by detecting the pattern recognized from a prior event.

Embodiments further provide power management enhancements over prior art devices. Some embodiments enable the entire wearable health sensor 100 only when a portion of the sensor 100 that is always left on detects certain patterns. Still other embodiments take readings at predetermined intervals and only take constant readings on the detection of an event or at the request of the user. Still even other embodiments provide intelligent power control based on the detection of various biometric events.

Embodiments provide specific methods for detecting particular conditions.

Embodiments provide no application or user interface, relying on an API that is made public to allow companies to buy the sensor 100 and create their own program to interface with the sensor(s) 100.

Even other embodiments provide local views and global views as well as historical data for comparison.

Still other embodiments utilize smartphone or integrated Global Positioning System (GPS) tracking capability, which may include geofencing capabilities, to track the user and take certain location-based actions and ascertain data that could not otherwise be obtained or validate data obtained by the sensors (e.g. distance walked, which could be measured by an accelerometer assuming a certain distance per stride via dead reckoning and confirmed by GPS).

Still even other embodiments group multiple 3-lead patches 100, allowing the system to perform as a 6 or 12 lead ECG. In embodiments, such patches 100 may perform arrhythmia detection using appropriate algorithms. In some cases, the sensors 100 are configured to provide sufficient data to external resources to allow for arrhythmia detection to be performed and such detection is done in post-processing.

Embodiments provide the sensor 100 as a biosensor patch, foam cardiac patch, and/or a tabled-plastic-encased wearable sensor 100.

Possible detection types include heart rate and heart rate variability, steps taken, respiratory rate, blood oxygen levels, skin temperature, body posture, glucose levels, fall detection, and GSR/EDA detection (change in amount of sweat in sweat glands).

From data taken in, embodiments are able to provide stress, energy expenditure (caloric burn), sleep quality, and contextual heart rate.

Components of various embodiments include the sensor 100, a microchip, a single-lead ECG, and a battery.

The foregoing description of the embodiments of the invention has been presented for the purposes of illustration and description. Each and every page of this submission, and all contents thereon, however characterized, identified, or numbered, is considered a substantive part of this application for all purposes, irrespective of form or placement within the application. This specification is not intended to be exhaustive or to limit the invention to the precise form disclosed. Many modifications and variations are possible in light of this disclosure.

The invention claimed is:

1. A wearable health monitor comprising:
at least one active sensor configured to emit a signal comprising electromagnetic radiation or electrical energy into a user and to measure a change in the signal, wherein said change in the signal corresponds to a first type of a biometric data;
at least one passive sensor configured to measure a biometric signal of the user, said biometric signal corresponding to a second type of the biometric data; and
a synchronization multiplexer configured to analyze the biometric signal from said passive sensor for repeating segments, determine which portion or portions of the repeating segments of the biometric signal are relatively constant, and synchronize outputs from said at least one active sensor such that an impact of those outputs on the second type of the biometric data received by said at least passive sensor is minimized by assigning periods of the emitted signal by the active sensor to the repeating segments of the biometric signal being measured by the passive sensor that are relatively constant,
wherein the signal emitted from the active sensor, if the signal emitted during the measurement of the biometric signal by the passive sensor, would result in interference,
wherein said at least one active sensor and said at least one passive sensor reside on a unitary patch, and
wherein said at least one active sensor is assigned at least one time slot in which to transmit the signal that corresponds with a repeating period of relatively-constant signal reception by said at least one passive sensor, wherein the relatively-constant signal received by said passive sensor is the biometric signal not transmitted by said active sensor.

2. The wearable health monitor of claim 1 wherein said synchronization multiplexer employs a multiplexing schema selected from a group consisting of Frequency Division Multiple Access (FDMA), Code Division Multiple Access (CDMA), Orthogonal Frequency Division Multiple Access (OFDMA), Time Division Multiple Access (TDMA), and Spatial Division Multiple Access (SDMA).

3. The wearable health monitor of claim 1 further comprising a wireless network connected-device configured to wirelessly connect said wearable health monitor to a wireless network and thereby enable sharing of the biometric data generated by said wearable health monitor.

4. The wearable health monitor of claim 3 wherein said wireless network connected-device is selected from a group consisting of a Bluetooth® module, an 802.1 1x wireless module, a cellular modem, and a Near Field Communication module.

5. The wearable health monitor of claim 4 wherein said wireless network connected-device is configured to allow said wearable health monitor to connect to a user device.

6. The wearable health monitor of claim 5 wherein said user device is a cellular phone.

7. The wearable health monitor of claim 1 wherein said at least one active sensor comprises an Electro Dermal Activity (EDA) sensor.

8. The wearable health monitor of claim 1 wherein said wearable health monitor is configured to monitor heart rate, heart rate variability, steps taken, respiratory rate, blood oxygen levels, skin temperature, body posture, and galvanic skin response/electro dermal activity.

9. The wearable health monitor of claim 1 wherein said wearable health monitor further comprising a power source that is charged through inductive charging.

10. The wearable health monitor of claim 1 further comprising an event button.

11. The wearable health monitor of claim 10 wherein said event button is configured, when activated, to perform a function selected from a group consisting of record the biometric data, alert emergency responders, and mark the recorded biometric data being recorded at that time for later review.

12. The wearable health monitor of claim 10 wherein said event button is configured to be triggered remotely, through a smartphone application.

13. A system of wearable health monitors comprising:
at least two wearable health monitors of the wearable health monitors, each monitor of the wearable health monitors comprising:
at least one active sensor configured to emit a signal comprising electromagnetic radiation or electrical energy into a user and to measure a change in the signal, wherein said change in the signal corresponds to a first type of a biometric data:
at least one passive sensor configured to measure a biometric signal of the user, said biometric signal corresponding to a second type of the biometric data: and
a synchronization multiplexer configured to analyze the biometric signal from said passive sensor for repeating segments, determine which portion or portions of the repeating segments of the biometric signal are relatively constant, and synchronize outputs from said at least one active sensor such that an impact of those outputs on the second type of the biometric data received by said at least passive sensor is minimized by assigning periods of the emitted signal by the active sensor to the repeating segments of the biometric signal being measured by the passive sensor that are relatively constant, wherein the signal emitted from the active sensor, if the emitted signal during the measurement of the biometric signal by the passive sensor, would result in interference, wherein at least one first wearable health monitor of the at least two wearable health monitors is configured to transmit a second signal, during use, through a body of the user using skin contact sensors that are configured to create a tissue pathway to a receiver, and at least one second wearable health monitor of the at least two wearable health monitors is configured to receive said second signal, wherein said at least one active sensor and said at least one passive sensor reside on a unitary patch, and wherein said at least one active sensor is assigned at least one time slot in which to transmit the signal that corresponds with a repeating period of relatively-constant signal reception by said at least one passive sensor, wherein the relatively-constant signal received by said passive sensor is the biometric signal not transmitted by said active sensor.

14. The system of wearable health monitors of claim 13 wherein the at least two wearable health monitors are configured to self-configure, as master/slave nodes or peer to peer nodes, dependent on network requirements.

15. The system of wearable health monitors of claim 13 wherein said at least two health monitors are configured to gather overlapping the biometric data, to compare said overlapping the biometric data, and to normalize said overlapping the biometric data by omitting erroneous data and averaging non-erroneous data from the biometric data.

16. The system of wearable health monitors of claim 13 further comprising a wideband noise sensor.

17. The system of wearable health monitors of claim 13 wherein said system comprises at least 5 wearable health monitors of the wearable health monitors and wherein said at least 5 wearable health monitors are configured to provide reverse phase noise cancellation functionality.

18. A method of monitoring biometric data in a patient comprising:

using a wearable health monitor comprising:
at least one active sensor configured to emit a signal comprising electromagnetic radiation or electrical energy into the patient and to measure a change in the signal, wherein said change in the signal corresponds to a first type of the biometric data;

at least one passive sensor configured to measure a biometric signal of the patient, said biometric signal corresponding to a second type of the biometric data; and a synchronization multiplexer configured to analyze the biometric signal from said passive sensor for repeating segments, determine which portion or portions of the repeating segments of the biometric signal are relatively constant, and synchronize outputs from said at least one active sensor such that an impact of those outputs on the second type of the biometric data received by said at least passive sensor is minimized by assigning periods of the emitted signal by the active sensor to the repeating segments of the biometric signal being measured by the passive sensor that are relatively constant, wherein the signal emitted from the active sensor, if the signal emitted during the measurement of the biometric signal by the passive sensor, would result in interference, monitoring the second type of the biometric data of the patient using said passive sensor;

determining repeating time periods where the biometric signal received by said passive sensor is relatively constant;

assigning said active sensor to the repeating time periods where the biometric signal received by said passive sensor is relatively constant;

using said active sensor, said emitting the signal comprising the electromagnetic radiation or electrical energy into the patient; and said measuring the change in said signal emitted by said active sensor, wherein said at least one active sensor and said at least one passive sensor reside on a unitary patch, and wherein said at least one active sensor is assigned at least one time slot in which to transmit the signal that corresponds with a repeating period of relatively-constant signal reception by said at least one passive sensor, wherein the relatively-constant signal received by said passive sensor is the biometric signal not transmitted by said active sensor.

\* \* \* \* \*